United States Patent
Luchetti et al.

(10) Patent No.: US 6,679,263 B2
(45) Date of Patent: Jan. 20, 2004

(54) AUTOMATIC HIGH TEMPERATURE VENTING FOR INFLATABLE MEDICAL DEVICES

(75) Inventors: Cynthia Luchetti, San Diego, CA (US); James Brown, Costa Mesa, CA (US)

(73) Assignee: LMA International, S.A., Channel Islands (GB)

( * ) Notice: Subject to any disclaimer, the term of this patent is extended or adjusted under 35 U.S.C. 154(b) by 0 days.

(21) Appl. No.: 10/201,399

(22) Filed: Jul. 23, 2002

(65) Prior Publication Data

US 2003/0230309 A1 Dec. 18, 2003

Related U.S. Application Data

(60) Provisional application No. 60/389,599, filed on Jun. 18, 2002.

(51) Int. Cl.[7] ............................................. A61M 16/00
(52) U.S. Cl. ................................................ 128/207.15
(58) Field of Search ..................... 128/200.24, 200.26, 128/207.14, 207.15, 202.24; 604/99.01, 99.02, 99.03

(56) References Cited

U.S. PATENT DOCUMENTS

| | | | | |
|---|---|---|---|---|
| 3,129,784 A | * | 4/1964 | Small peice ................ | 181/237 |
| 3,402,718 A | * | 9/1968 | Doherty .................. | 128/207.15 |
| 3,460,541 A | * | 8/1969 | Doherty .................. | 128/207.15 |
| 3,468,471 A | * | 9/1969 | Linder ...................... | 206/439 |
| 3,504,676 A | * | 4/1970 | Lomholt ................. | 128/207.15 |
| 3,613,732 A | | 10/1971 | Willson et al. ......... | 137/625.44 |
| 3,845,931 A | | 11/1974 | Pimentel ..................... | 251/11 |
| 3,918,221 A | * | 11/1975 | Benjamin ....................... | 52/1 |
| 3,974,844 A | | 8/1976 | Pimentel ........................ | 137/1 |
| 3,985,141 A | * | 10/1976 | Stanley et al. .......... | 128/207.15 |
| 4,068,820 A | | 1/1978 | Pimentel ..................... | 251/11 |
| 4,116,201 A | * | 9/1978 | Shah ...................... | 128/207.15 |
| 4,147,170 A | * | 4/1979 | Taylor .................... | 128/207.15 |
| 4,159,722 A | * | 7/1979 | Walker ....................... | 137/496 |
| 4,177,863 A | * | 12/1979 | Simon .......................... | 169/62 |
| 4,178,938 A | * | 12/1979 | Au .......................... | 128/207.15 |
| 4,182,344 A | * | 1/1980 | Benson ................... | 128/207.15 |

(List continued on next page.)

*Primary Examiner*—Aaron J. Lewis
(74) *Attorney, Agent, or Firm*—Hale and Dorr LLP

(57) ABSTRACT

The disclosed medical device includes an inflatable structure configured for positioning in an airway of a human patient and a valve in fluid communication with the inflatable structure. The valve includes a member that is movable between an open position and a closed position. The valve prevents fluid from escaping the inflatable structure when the member is in the closed position. The valve permits fluid to escape the inflatable structure when the member is in the open position. The valve includes a resilient element. The resilient element provides a first force that biases the member towards the closed position. The valve includes a temperature sensitive element. The temperature sensitive element generates a second force that biases the member towards the open position. The first force is greater than the second force when the ambient temperature is below a first value. The first force is smaller than the second force when the ambient temperature is above a second value.

36 Claims, 8 Drawing Sheets

U.S. PATENT DOCUMENTS

| | | | |
|---|---|---|---|
| 4,228,914 A | * 10/1980 | Sanderson | 220/203.15 |
| 4,247,517 A | * 1/1981 | Sanderson et al. | 422/26 |
| 4,248,222 A | * 2/1981 | Jaeger et al. | 128/207.15 |
| 4,251,482 A | * 2/1981 | Sanderson et al. | 422/26 |
| 4,501,273 A | * 2/1985 | McGinnis | 128/207.15 |
| 4,509,514 A | * 4/1985 | Brain | 128/207.15 |
| 4,523,605 A | 6/1985 | Ohkata | 137/62 |
| 4,645,489 A | 2/1987 | Krumme et al. | 604/65 |
| 4,841,730 A | 6/1989 | McDonald | 60/527 |
| 5,065,757 A | * 11/1991 | Dragisic et al. | 128/207.14 |
| 5,211,371 A | 5/1993 | Coffee | 251/11 |
| 5,261,597 A | 11/1993 | Perlman et al. | 236/93 |
| 5,788,212 A | 8/1998 | Hackman et al. | 251/11 |
| 6,079,413 A | 6/2000 | Baran | 128/207.14 |
| 6,090,083 A | 7/2000 | Sell et al. | 604/249 |
| 6,110,143 A | * 8/2000 | Kamen | 604/97.02 |
| 6,374,608 B1 | 4/2002 | Corris et al. | 60/528 |
| 6,382,207 B1 | * 5/2002 | Giuffre et al. | 128/202.24 |

* cited by examiner

US 6,679,263 B2

AUTOMATIC HIGH TEMPERATURE VENTING FOR INFLATABLE MEDICAL DEVICES

BACKGROUND OF THE INVENTION

The present invention relates to inflatable medical devices. More specifically, the present invention relates to protecting medical devices during sterilization by providing automatic venting at high temperatures.

The laryngeal mask airway device is a well known device that is useful for establishing airways in unconscious patients. FIG. 1 shows a perspective view of a prior art laryngeal mask airway device 100. Laryngeal mask airway devices such as device 100 are described for example in U.S. Pat. No. 4,509,514. Device 100 includes a hollow airway tube 110 and an inflatable mask portion 130. Tube 110 extends from a proximate end 112 to a distal end 114 and defines an interior airway lumen that extends through the tube from the proximate end 112 to the distal end 114. Mask portion 130 defines, at least when inflated, a central opening 136. Mask portion 130 is coupled to the airway tube such that the lumen of the airway tube communicates with the mask portion's central opening and such that the device 100 provides a sealed internal passage that extends from the proximate end 112 to opening 136.

In operation, the mask portion 130 is deflated, and then the mask portion is inserted through a patient's mouth into the patient's pharynx. The mask portion is preferably positioned so that a distal end 140 of mask portion 130 rests against the patient's normally closed esophagus and so that the opening 136 of the mask portion 130 is aligned with the entryway of the patient's trachea (i.e., the patient's glottic opening). After the mask portion is so positioned, the mask portion is inflated thereby forming a seal around the patient's glottic opening and this establishes a sealed airway extending from the proximate end 112 of the tube 110 to the patient's trachea. The proximate end 112, which remains outside the patient, may be coupled to a ventilator for providing ventilation to the patient's lungs.

Referring again to FIG. 1, laryngeal mask airway device 100 also includes an inflation tube 138 for permitting selective inflation or deflation of mask portion 130. An inflation valve 150 is connected to the proximate end of the inflation tube 138 and the distal end of inflation tube 138 is connected to the mask portion. The inflation valve 150 is normally closed so as to maintain the current pressure in mask portion 130. However, valve 150 may be opened to permit inflation or deflation mask portion 130.

FIG. 2A shows a sectional view of inflation valve 150, when the valve is closed (or when fluid may not freely flow between a first end 152 of the valve and a second end 154 of the valve). FIG. 2B shows a sectional view of inflation valve 150, when the valve is open (or when fluid may freely flow between first and second ends 152, 154). FIG. 2C shows a view of the first end 152 of valve 150 taken in the direction of arrow 2C—2C as shown in FIG. 2A. FIG. 2D shows an exploded sectional view of inflation valve 150, in which, for convenience of illustration, the space between opposite sectional views of body 160 has been artificially enlarged. FIG. 2E shows a more detailed sectional view of a typical prior art inflation valve 150, when the valve is closed.

As shown, inflation valve 150 includes a hollow body 160, which defines a central channel 169 that extends entirely through the body from end 152 to end 154. Valve 150 also includes a movable member, or pin, 170, and a spring 180, both of which are disposed within the central channel 169 of hollow body 160. One end 182 of spring 180 contacts a shoulder 162 of body 160. The other end 184 of spring 180 contacts a shoulder 172 of pin 170. The spring biases pin 170 away from shoulder 162 (or upwards as shown in FIGS. 2A, 2B, and 2D) such that a shoulder 174 of pin 170 normally contacts a shoulder 164 of body 160.

In the normal resting position of valve 150 (shown in FIG. 2A), contact between shoulder 174 (of pin 170) and shoulder 164 (of body 160) forms a seal and effectively prevents fluid from passing through channel 169 between the first end 152 and the second end 154 of valve 150 thereby closing the valve. The position of pin 170 shown in FIG. 2A may be regarded as a "closed position". As shown in FIG. 2B, valve 150 may be opened by biasing pin 170 such that shoulder 174 (of pin 170) is separated from shoulder 164 (of body 160). Valve 150 is "open" as soon as shoulders 174 and 164 separate from one another. Once valve 150 is open, fluid may pass through channel 169 between the first end 152 and the second end 154 of valve 150 (i.e., fluid may pass from the first end to the second end or from the second end to the first end depending upon relative pressures at the valve ends). Any position of pin 170 in which shoulder 174 (of pin 170) is separated from shoulder 164 (of body 160) may be regarded as an "open position". If biasing of pin 170 continues, a shoulder 176 (of pin 170) eventually contacts a shoulder 166 (of body 160). Shoulder 166 serves to limit the motion of pin 170 such that once shoulders 176 and 166 contact one another, further movement of pin 170 (in a direction that continues to separate shoulders 174 and 164 from one another) is prevented. Unlike shoulders 174 and 164, the shoulders 176 and 166 do not form sealing surfaces, such that valve 150 is open even when shoulders 176 and 166 are in contact.

In laryngeal mask airway devices, the second end 154 of valve 150 is normally connected to the inflation line 138 (shown in FIG. 1). The valve 150 is normally closed so that if the mask portion 130 is inflated or pressurized, valve 150 maintains the pressure in the mask portion, or prevents gas in mask portion 130 from passing through valve 150 and escaping to the atmosphere external to the device. In its normally closed position, valve 150 also prevents mask portion 130 from spontaneously inflating after mask portion 130 has been intentionally deflated. Although it is normally closed, valve 150 may be temporarily opened to permit selective inflation and deflation of mask portion 130. Normally, an air syringe, or other air supply device (not shown), is coupled to end 152 of valve 150, and in the act of coupling, the air supply device biases the pin 170 so as to separate shoulders 174 (of pin 170) and 164 (of body 160) and thereby open the valve. The air supply device may then inflate or deflate mask portion 130. Once the air supply device is decoupled from valve 150, the biasing force provided by spring 180 automatically closes valve 150 and thereby maintains the current pressure inside of mask portion 130. End 152 of valve 150 is normally designed to comply with International Standard ISO 594-1 so that it may readily be coupled to standard air supply devices.

Although valves such as valve 150 have been in use for many years and have functioned well, there remains a need for providing improved control over the pressure in the inflatable portions of laryngeal mask airway devices as well as in other inflatable devicies.

SUMMARY OF THE INVENTION

These and other objects are provided by improved inflation valves and by inflatable devices constructed using those valves.

Several varieties of laryngeal mask airway devices are durable enough to permit them to be sterilized in an autoclave and reused. For example, the "Classic" laryngeal mask airway device sold by the Laryngeal Mask Company of Cyprus, is guaranteed to survive forty sterilizations, and in practice these devices may generally be sterilized (and reused) more than forty times before becoming too worn for reuse. The "Proseal", also sold by the Laryngeal Mask Company of Cyprus, may also be sterilized and reused.

The sterilization process normally involves exposing the laryngeal mask airway device to a high temperature environment inside an autoclave. The pressure of the environment inside an autoclave typically varies during the sterilization process such that at times the pressure is relatively high and at other times the pressure is relatively low. Laryngeal mask airway devices are normally fully deflated before being placed inside an autoclave for sterilization. If the devices are not fully deflated prior to sterilization, air trapped inside the mask portion can cause the mask portion to expand when the environment inside the autoclave is at a low pressure. Such expansion can sometimes cause the mask portion to burst thereby rendering the laryngeal mask airway device useless. Also, even if the mask portion doesn't burst, excessive expansion of the mask portion within an autoclave may weaken or permanently deform the mask portion thereby decreasing the device's useful life or potentially reducing the device's usefulness.

One problem with prior art laryngeal mask airway devices is that practitioners cannot be relied upon to deflate them sufficiently to prevent potentially damaging expansion of the mask portion during sterilization in an autoclave. Also, if a laryngeal mask airway device is exposed to normal atmospheric pressure for several hours after a full deflation, the semi-permeable nature of most mask portions allow them to partially inflate. Such partial inflation can also result in potentially damaging expansion of the mask portion during subsequent sterilization. These problems are most serious for laryngeal mask airway devices that use a relatively soft material for the mask portion (e.g., such as the Proseal). However, the problem potentially affects any reusable (i.e., sterilizable) inflatable device.

The invention provides improved inflation valves and inflatable devices constructed with such valves. Valves constructed according to the invention automatically open when exposed to high temperatures. Accordingly, when a laryngeal mask airway device, or other inflatable device (such as an endotracheal tube, a tracheostomy tube, or a balloon catheter), equipped with a valve constructed according to the invention is sterilized, the valve will advantageously automatically open when exposed to the high temperature environment of the autoclave. This allows any gas that may have been previously trapped in the inflated portion of the device to escape through the valve into the autoclave chamber during low pressure portions of the sterilization process. Valves constructed according to the invention thereby automatically protect the inflatable portion of medical devices from undue expansion and wear.

In one aspect, the invention provides a laryngeal mask airway device comprising an airway tube, an inflatable mask portion, and a valve. The airway tube can extend from a proximate end, to a distal end. The inflatable mask portion can be fixed to the airway tube. The mask portion can be insertable through the mouth of a patient to an inserted location within the patient. The mask portion can form a seal around the patient's glottic opening when the mask portion is in the inserted location and inflated. The proximate end of the airway tube can be disposed outside the patient when the mask portion is in the inserted location. The valve can be in fluid communication with the inflatable mask portion. The valve can include a member that is movable between an open position and a closed position. The valve can prevent fluid from escaping the mask portion when the member is in the closed position. The valve can permit fluid to escape the mask portion when the member is in the open position. The valve can include a resilient element. The resilient element can provide a first force that biases the member towards the closed position. The valve can include a temperature sensitive element. The temperature sensitive element can generate a second force that biases the member towards the open position. The first force can be greater than the second force when the ambient temperature is below a first value. The first force can be smaller than the second force when the ambient temperature is above a second value. An end portion of the member can be accessible to an environment external to the valve. The member can be movable to the open position by applying pressure to the end portion of the member.

In this aspect, the second force can be substantially equal to zero when the ambient temperature is below the first value.

Also in this aspect, the temperature sensitive element can comprise a nickel titanium alloy.

Also in this aspect, the temperature sensitive element can be characterized by a first length when the ambient temperature is below the first value, and the temperature sensitive element can be characterized by a second length when the ambient temperature is above the second value, the first length being longer than the second length.

Also in this aspect, the valve can include a body, the body defining an internal passage that extends through the body. Also, the body can further define a first shoulder. Also, the member can define a second shoulder, the first and second shoulders being in contact when the member is in the closed position, the first and second shoulders being spaced apart when the member is in the open position. Also, the device can include a cap fixed to one end of the body. Also, the device can include a post fixed to one end of the member. Also, the temperature sensitive element can have a first end, a second end, and a central portion, the first and second ends of the temperature sensitive element being fixed to the cap, the central portion of the temperature sensitive element contacting the post. Also, the post can define a slot, the central portion of the temperature sensitive element extending through the slot. Also, the cap can include a base, a body, and at least one clamp. Also, the clamp can be disposed between a portion of the base and a portion of the body. Also, an end of the temperature sensitive element can be fixed to the clamp. Also, the member can be disposed in the internal passage. Also, an end of the member can be proximate to an open end of the valve. Also, the second value can be greater than or equal to seventy degrees Celsius.

In another aspect, the invention provides a medical device comprising a tube, an inflatable structure, an inflation lumen, and a valve. The tube can define an interior passage. The inflatable structure can be fixed to the tube. The inflatable structure can be insertable into an airway of a human patient. The inflatable structure can form a seal with a portion of the airway when inserted into the patient and inflated. The inflation lumen can have a first end and a second end. The first end of the inflation lumen can be coupled to the inflatable structure. The valve can be coupled to the second end of the inflation lumen. The valve can define a closed position and an open position. A fluid flow path can be provided when the valve is in the open position, the fluid flow path extending from an interior of the inflatable structure through the inflation lumen and through the valve. The valve can block the fluid flow path when the valve is in the closed position. The valve can include a temperature sensitive element. The temperature sensitive element can force the valve into the open position when a temperature exceeds a first value. The temperature sensitive element can allow the valve to return to the closed position when the temperature falls below a second value.

In this aspect, the valve can include a movable member and a body, a first surface of the movable member contacting a second surface of the body when the valve is in the closed position, the first surface of the movable member being spaced apart from the second surface of the body when the valve is in the open position. Also, the valve can include a spring, the spring biasing the first surface of the movable member towards the second surface of the body.

In another aspect, the invention provides a method of automatically protecting an inflatable device during sterilization. The method can include a step of providing the device with a temperature sensitive valve that automatically opens when a temperature exceeds a first value. The method can further include a step of exposing the device to an environment that will sterilize the device, the environment being characterized by a temperature above the first value. When the temperature exceeds the first value, the valve can automatically open and permit fluid in the inflatable device to escape into the environment.

In another aspect, the invention provides a medical device including an inflatable structure and a valve. The inflatable structure can be configured for positioning in a human patient. The valve can be in fluid communication with the inflatable structure. The valve can include a member that is movable between an open position and a closed position. The valve can prevent fluid from escaping the inflatable structure when the member is in the closed position. The valve can permit fluid to escape the inflatable structure when the member is in the open position. The valve can include a resilient element. The resilient element can provide a first force that biases the member towards the closed position. The valve can include a temperature sensitive element. The temperature sensitive element can generate a second force that biases the member towards the open position. The first force can be greater than the second force when the ambient temperature is below a first value. The first force can be smaller than the second force when the ambient temperature is above a second value. An end portion of the member can be accessible to an environment external to the valve. The member can be movable to the open position by applying pressure to the end portion of the member.

In this aspect, the second force can be substantially equal to zero when the ambient temperature is below the first value.

Also in this aspect, the temperature sensitive element can comprise a nickel titanium alloy.

Also in this aspect, the temperature sensitive element can be characterized by a first length when the ambient temperature is below the first value, and the temperature sensitive element can be characterized by a second length when the ambient temperature is above the second value. The first length can be longer than the second length.

Also in this aspect, the valve can include a body. The body can define an internal passage that extends through the body. Also, the body can define a first shoulder. Also, the member can define a second shoulder. The first and second shoulders can be in contact when the member is in the closed position.

The first and second shoulders can be spaced apart when the member is in the open position. Also, the device can include a cap fixed to one end of the body. Also, the device can include a post fixed to one end of the member. Also, the temperature sensitive element can have a first end, a second end, and a central portion. The first and second ends of the temperature sensitive element can be fixed to the cap. The central portion of the temperature sensitive element can contact the post. Also, the post can define a slot. The central portion of the temperature sensitive element can extend through the slot. Also, the cap can include a base, a body, and at least one clamp. Also, the clamp can be disposed between a portion of the base and a portion of the body. Also, the end of the temperature sensitive element can be fixed to the clamp. Also, the second value can be greater than or equal to seventy degrees Celsius.

Still other objects and advantages of the present invention will become readily apparent to those skilled in the art from the following detailed description wherein several embodiments are shown and described, simply by way of illustration of the best mode of the invention. As will be realized, the invention is capable of other and different embodiments, and its several details are capable of modifications in various respects, all without departing from the invention. Accordingly, the drawings and description are to be regarded as illustrative in nature, and not in a restrictive or limiting sense, with the scope of the application being indicated in the claims.

BRIEF DESCRIPTION OF THE FIGURES

For a fuller understanding of the nature and objects of the present invention, reference should be made to the following detailed description taken in connection with the accompanying drawings in which the same reference numerals are used to indicate the same or similar parts wherein.

DETAILED DESCRIPTION OF THE PREFERRED EMBODIMENTS

Figure 3A:
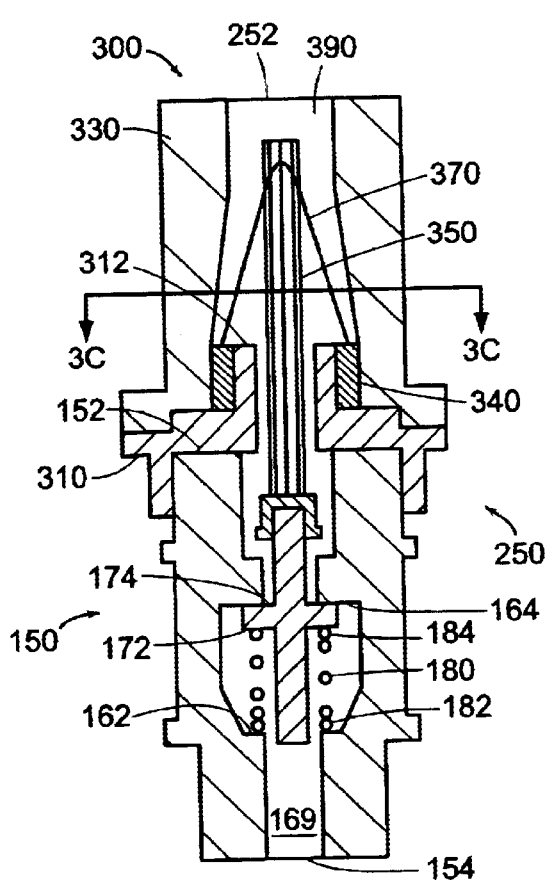
FIG. 3A shows a sectional view of an inflation valve constructed according to the invention in its normally closed position.
Figure 3B:
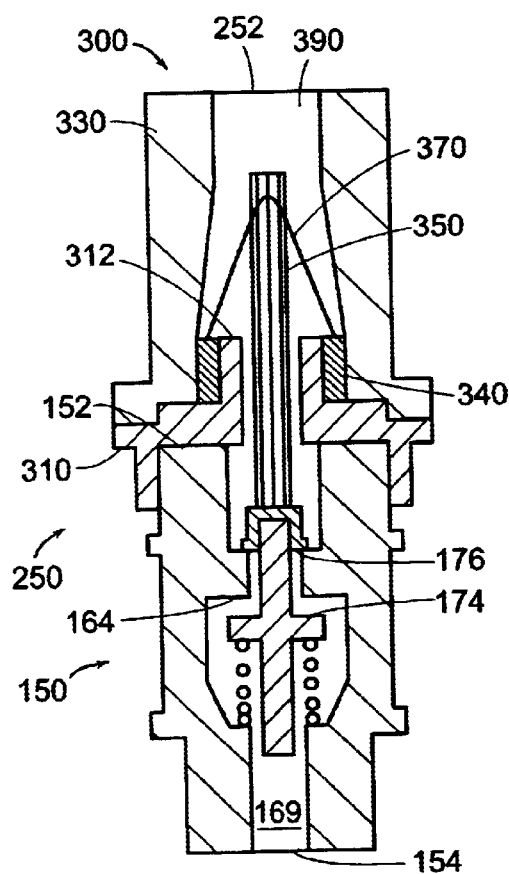
FIG. 3B shows a sectional view of the valve shown in FIG. 3A in an open position.
Figure 3C:
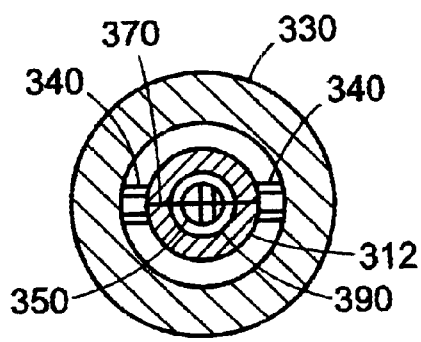
FIG. 3C shows a view of the valve taken in the direction of arrow 3C—3C as shown in FIG. 3A.

FIG. 3A shows a sectional view of a valve 250 constructed according to the invention in its normally closed position (i.e., a position in which valve 250 prevents fluid from flowing between ends 154 and 252 of valve 250 or at least provides resistance to fluid flowing between ends 252 and 154). FIG. 3B shows a sectional view of valve 250 in an open position (i.e., a position in which valve 250 permits fluid to flow between ends 154 and 252 of valve 250). FIG. 3F shows a more detailed sectional view of a valve constructed according to the invention.

When exposed to normal room temperatures, valve 250 is normally in the closed position shown in FIG. 3A. When exposed to high temperatures, valve 250 automatically transitions to an open position such as that shown in FIG. 3B. Valve 250 may of course also be opened manually, even at room temperatures, for example by coupling an air supply device, such as a syringe (not shown), to end 252 of valve 250. End 252 of valve 250 may be configured so as to comply with International Standard ISO 594-1 to facilitate coupling to standard air supply devices.

Figure 2A:
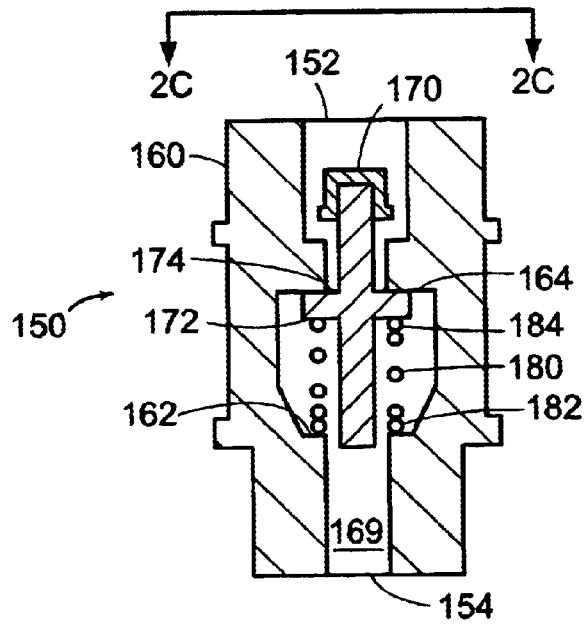
FIG. 2A shows a sectional view of a prior art inflation valve, used with laryngeal mask airway devices, in its normally closed position.
Figure 2B:
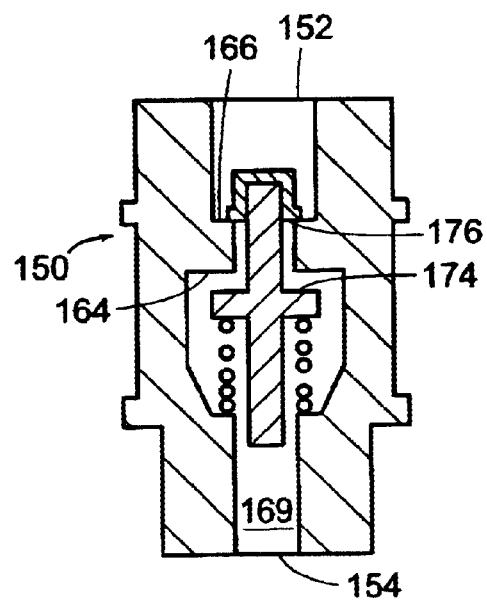
FIG. 2B shows a sectional view of the valve shown in FIG. 2A in an open position.
Figure 2C:
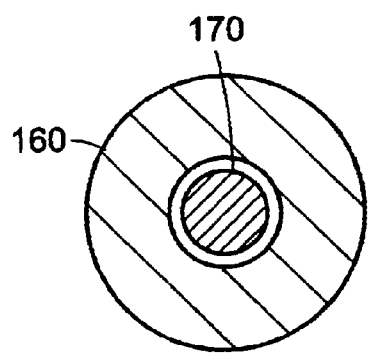
FIG. 2C shows a view of the valve taken in the direction of arrow 2C—2C as shown in FIG. 2A.
Figure 2D:
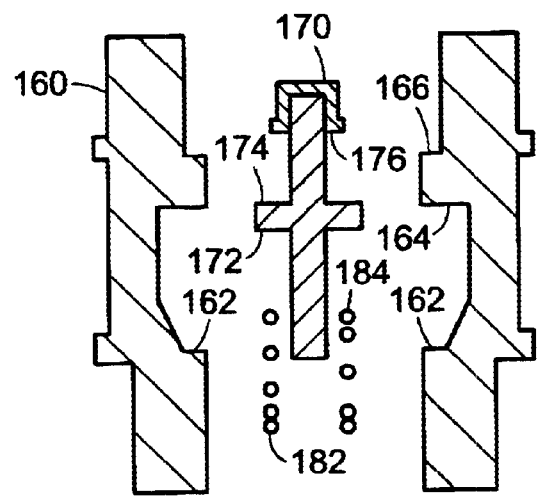
FIG. 2D shows a sectional view of the valve shown in FIGS. 2A–2C in which sectional views of the body are artificially expanded.
Figure 2E:
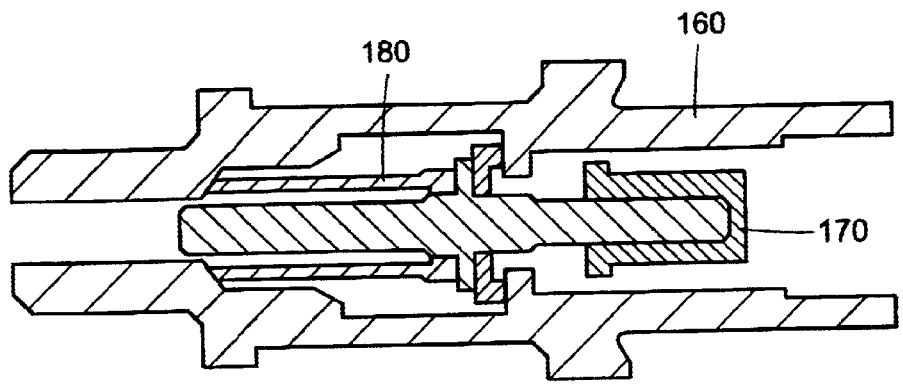
FIG. 2E shows a more detailed sectional view of a prior art inflation valve of the type generally illustrated in FIGS. 2A–2D.

As shown, valve 250 includes a prior art valve 150 (as shown in, e.g., in FIG. 2A) as well as a hollow cap 300, which is coupled to end 152 valve 150. Cap 300 includes a base 310, a body 330, and two clamps 340, and cap 300 defines a central channel 390. Valve 250 also includes a post 350 and a temperature sensitive wire 370 disposed in channel 390. FIG. 3C shows a view of cap 300 taken in the direction of arrow 3C—3C as shown in FIG. 3A.

As shown most clearly in FIGS. 3A and 3B, base 310 engages end 152 of prior art valve 150. Body 330 engages base 310, and clamps 340 are trapped, or clamped, between base 310 and body 330. More specifically, and as shown best in FIG. 3C, base 310 defines an annular extension 312, and clamps 340 are trapped between the outer wall of extension 312 and the inner wall of body 330. Base 310, body 330, and clamp 340 cooperate so that cap 300 effectively provides a relatively rigid structure that is fixed relative to valve 150 such that channel 390 of cap 300 communicates with channel 169 of body 160.

One end of post 350 is fixed to, or rests on, pin 170 of the prior art valve 150, and post 350 extends through hollow interior channel 390 towards end 252 of valve 250. The two ends of temperature sensitive wire 370 are fixed to, or held by, clamps 340, and the center of wire 370 is threaded through a slot 352 defined in post 350.

Figures 3D, 3E:
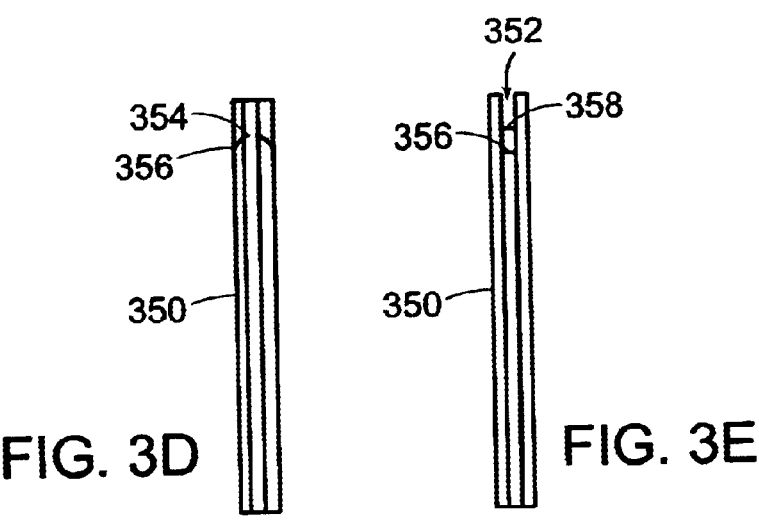
FIG. 3D shows the post of the valve shown in FIGS. 3A–3C prior to assembly into the valve.
FIG. 3E shows a view of the post that is rotated ninety degrees from the view shown in FIG. 3D.

FIGS. 3D and 3E show two views of post 350 (prior to its assembly into valve 250) and illustrate the slot 352 through which wire 370 is threaded. The view of post 350 shown in FIG. 3D is rotated ninety degrees from the view shown in FIG. 3E. The slot 352 is shown best in FIG. 3E. As shown in FIG. 3D, the floor 354 of the slot 352 defines a curved profile. The floor 354 of slot 352 has its lowest points 356 proximate to the outer perimeter of post 350 and has its highest point 358 near the center of post 350. A central portion of temperature sensitive wire 370 rests on the curved floor 354 of slot 352 as shown in FIG. 3A. Providing slot 352 with such a curved floor advantageously prevents wire 370 from contacting a "sharp corner" of post 350 and thereby reduces wear on temperature sensitive wire 370.

Temperature sensitive wire 370 is fabricated so that its length decreases when exposed to high temperatures and so that its length increases (or so that wire 370 returns to its original, or near original, un-contracted length) when exposed to normal room temperatures. As shown in FIG. 3B, when the length of wire 370 shrinks, it biases post 350 and thereby pushes pin 170 so as to compress spring 180 and thereby open valve 250. Since shoulders 174 (of pin 170) and 164 (of body 160) are separated from one another, the position of pin 170 and post 350 shown in FIG. 3B may be regarded as an open position. As shown in FIG. 3A, when the length of wire 370 increases (or returns to its original, or near original, un-contracted length), it allows spring 180 to bias pin 170 and post 350 upwards (in the orientation of valve 250 shown in FIG. 3A) to thereby close valve 250. The position of pin 170 and post 350 shown in FIG. 3A may be regarded as a closed position.

In its expanded condition, wire 370 may be under some amount of tension. As long as the resultant force (i.e., a force which is parallel to and opposite to the force generated by spring 180) generated by the wire 370 is smaller than the force generated by spring 180, the spring 180 can bias the pin 170 to a closed position thereby closing the valve. Alternatively, when wire 370 is in its expanded condition, it may define some slack so that the force applied by wire 370 to post 350 is nominal or effectively zero.

One preferred class of materials for fabricating temperature sensitive wire 370 are nickel titanium alloys. These materials, commonly known as NITINOL, possess a variety of unusual but well documented properties, including the ability to shrink or contract when heated and to expand when cooled. More specifically, these materials generally undergo a phase transformation in their crystal structure when cooled from a stronger, high temperature form (Austenite) to a weaker, low temperature form (Martensite). As such, these materials effectively provide two distinct configurations. Also, raising or lowering the temperature by just a few degrees is normally sufficient to cause the material to shift from one configuration to the other. In one preferred embodiment, (1) temperature sensitive wire 370 transitions from its low temperature phase (or its longer configuration in which valve 250 is closed) to its high temperature phase (or its shorter configuration in which valve 250 is open) at about seventy degrees Celsius and (2) temperature sensitive wire 370 transitions from its high temperature phase (or its shorter configuration in which valve 250 is open) to its low temperature phase (or its longer configuration in which valve 250 is closed) at about fifty degrees Celsius. Such hysteresis is common in nickel titanium alloys. Also, it will be appreciated that other temperature ranges could be used (e.g., ninety degrees Celsius, or a human body temperature, could alternatively be used as the temperature at which valve 250 transitions from its normally closed position to its open position). Also, wire 370 is preferably configured so that its length changes by about four percent when it changes from its low temperature phase to its high temperature phase.

At the room temperatures in which medical devices are normally used with patients, valve 250 is normally closed. However, even at room temperatures in which valve 250 is normally closed, valve 250 may be opened in the customary fashion, e.g., by coupling an air supply device such as an air syringe to one end of the valve, to permit inflation or deflation of the medical device. When a device such as an air syringe is coupled to the valve, the syringe depresses post 350 to open the valve. Depression of post 350 (e.g., by an air syringe) to open valve 250 is generally possible because an end of post 350 is accessible to the environment external to valve 250 (in a fashion similar to that in which an end of pin 170 is accessible to an environment external to prior art valve 150). Preferably, temperature sensitive element 370 fits loosely within slot 352 so that depression of post 350 by an air syringe does not cause significant movement of wire 370.

Figure 3I:
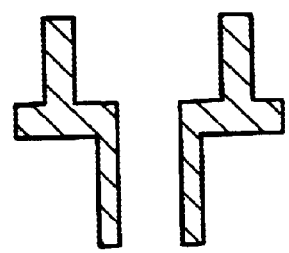
FIGS. 3I and 3H show side views of the base shown in FIG. 3G.
Figure 3H:
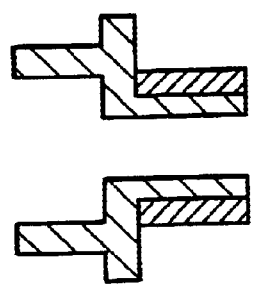
Figure 3G:
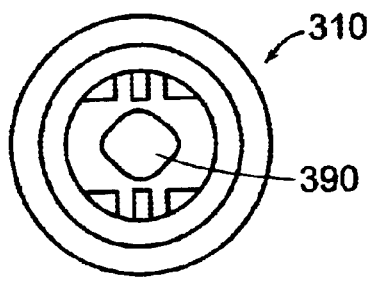
FIG. 3G shows an end view of one embodiment of the base shown generally in FIGS. 3A, 3B, and 3C.
Figure 3F:
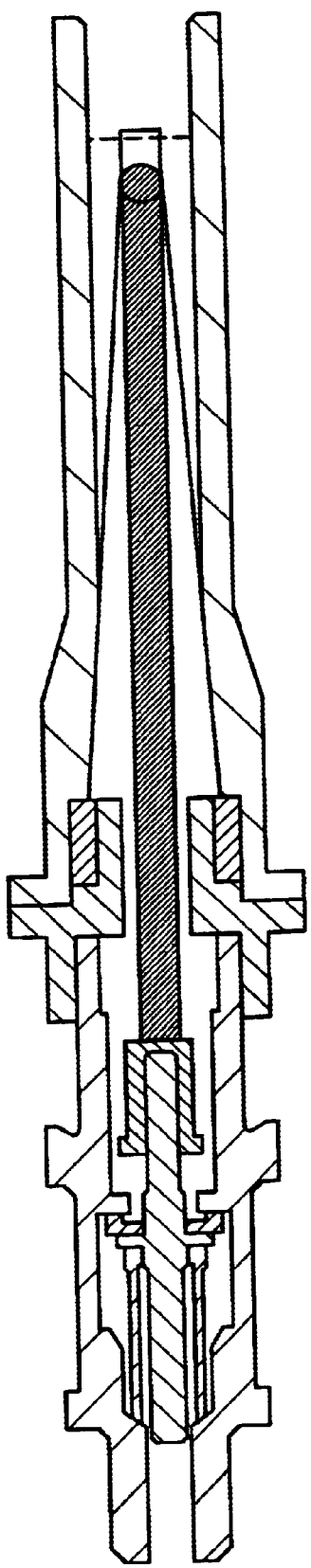
FIG. 3F shows a more detailed sectional view of a valve constructed according to the invention of the type generally illustrated in FIGS. 3A–3E.
Figure 3M:
FIGS. 3L and 3M show end and side views, respectively, of the post that are rotated ninety degrees from the views shown in FIGS. 3J and 3K.
Figure 3L:
Figure 3K:
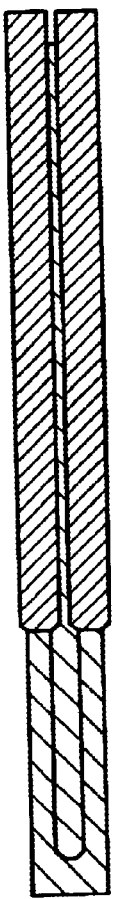
FIGS. 3J and 3K show end and side views, respectively, of one embodiment of the post shown generally in FIGS. 3A–3F.
Figure 3J:

Coupling or decoupling an air supply device to or from end 252 may cause some rotation of post 350. If post 350 is allowed to freely rotate with respect to base 310, such rotation may damage temperature sensitive element 370. Accordingly, it may be preferable to prevent post 350 from rotating with respect to base 310 or clamps 340. One way to prevent post 350 from rotating with respect to base 310 is to elongate the aperture of base 310 through which post 350 extends and to also elongate the cross section of post 350. FIGS. 3G–3M illustrate such a configuration of post 350 and base 310. More particularly, FIG. 3G shows an end view of one embodiment of base 310 in which the central channel 390, through which post 310 extends when the valve is assembled, is elongated. FIGS. 3H and 3I show two side views of base 310. FIGS. 3J-3M show different views of post 350. As shown, the cross section of the portion of post 350 that extends through base 310 is not circular and is instead elongated, or generally elliptical. When the valve is assembled, any substantial rotation (e.g., more than about 5 degrees) of post 350, will cause the post to contact the walls of the channel 390 defined by base 310 and thereby prevent post 350 from rotating further with respect to base 310.

Figure 4:
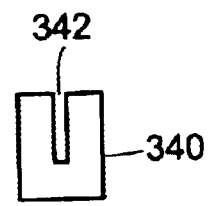
FIG. 4 shows one embodiment of a clamp for use with valves constructed according to the invention.

Clamps 340 may be metallic (e.g., fabricated from brass) and the post 350 and the components of cap 300 may be made from plastic. However, it will be appreciated that a variety of other materials may be used to fabricate valve 250. For example, the entire valve could be made of one or more metals such as aluminum. FIG. 4 shows one embodiment for fabricating clamp 340. In this embodiment, clamp 340 is a metallic block that defines a slot 342. During assembly, one end of temperature sensitive wire 370 is inserted into slot 342 and then clamp 340 is squeezed or crimped so that clamp 340 effectively anchors, or permanently holds onto, the end of wire 370. It will be appreciated however that many other methods and structures may be used for anchoring wire 370 to a fixed location in valve 250.

Figure 5A:
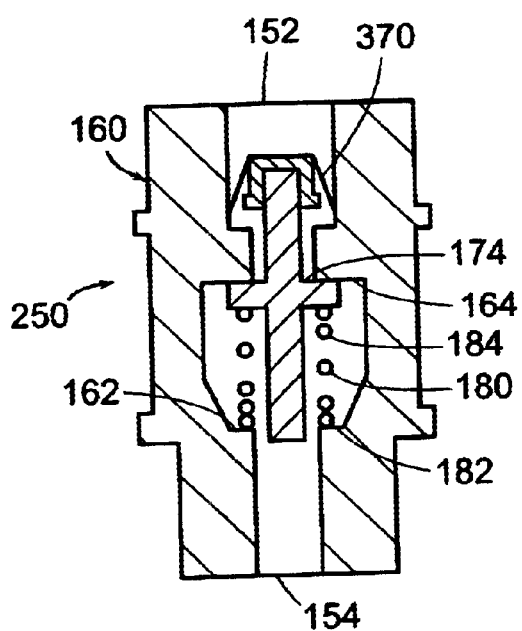
FIG. 5A shows a sectional view of another embodiment of an inflation valve constructed according to the invention in its normally closed position.
Figure 5B:
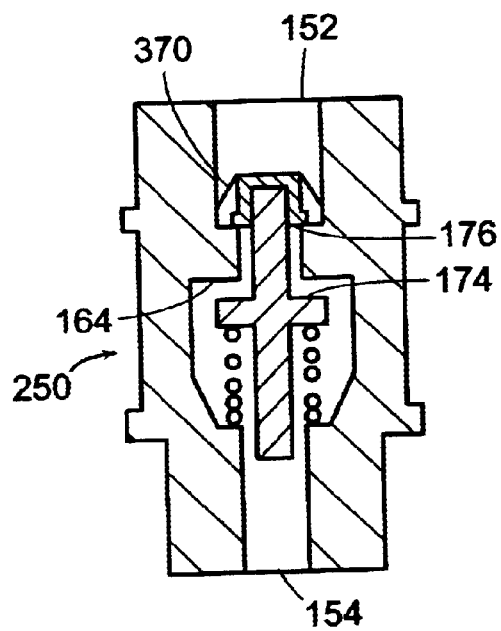
FIG. 5B shows a sectional view of the valve shown in FIG. 5A in an open position.

While the preferred embodiment of valve 250 includes a cap that is coupled to a standard prior art valve, as has been generally discussed above in connection with FIGS. 3A–3F, it will be appreciated that numerous other embodiments of valve 250 are embraced within the invention. FIGS. 5A and 5B illustrate an example of another embodiment of a valve 250 constructed according to the invention. In this embodiment, rather than using a cap for mounting temperature sensitive wire 370, the temperature sensitive wire 370 is fixed to the body 160 of the valve. FIG. 5A shows valve 250 in its normally closed position. FIG. 5B shows valve 250 when shrinkage of temperature sensitive wire 370, caused by exposure to high temperature, caused valve 250 to move into an open position.

Figure 6:
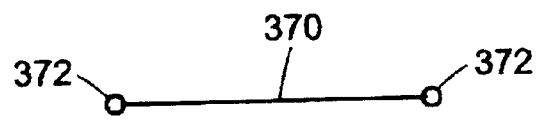
FIG. 6 shows one embodiment of a temperature sensitive element for use with valves constructed according to the invention.

It will be appreciated that the ends of a temperature sensitive wire 370 may be fixed, or anchored, to a structure such as body 160 in numerous ways such as by clamping, welding, adhesives, etc. Also, it may be advantageous to provide the ends of wire 370 with enlarged structures, or anchors, 372, as shown generally in FIG. 6. Including such anchors 372 may facilitate attachment of wire 370 to a structure such as clamp 340 or the body of a valve. It will further be appreciated that although a "wire" is a preferred configuration for temperature sensitive element 370, the temperature sensitive element 370 may be configured in other shapes and forms without departing from the invention.

Figure 7A:
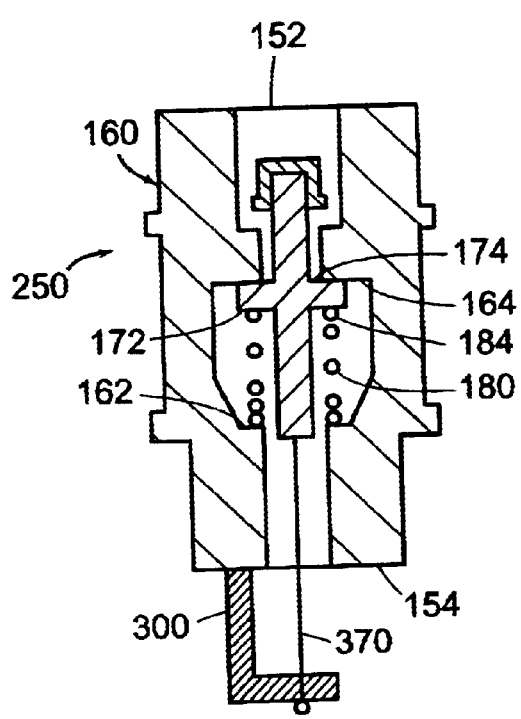
FIG. 7A shows a sectional view of another embodiment of an inflation valve constructed according to the invention in its normally closed position.
Figure 7B:
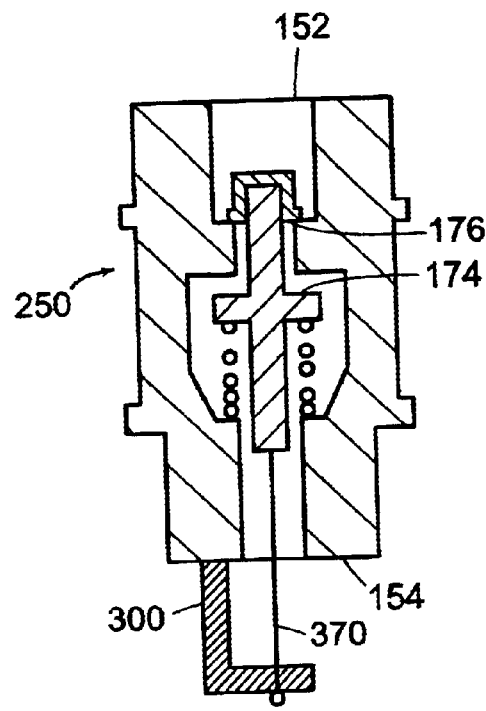
FIG. 7B shows a sectional view of the valve shown in FIG. 7A in an open position.

FIGS. 7A and 7B illustrate an example of yet another embodiment of a valve 250 constructed according to the invention. In this embodiment, rather than attaching a cap to end 152 (as shown for example in FIGS. 3A–3F), a simpler cap or L-bracket 300 is attached to end 154 of valve 250. Temperature sensitive element 370 is coupled between an end of bracket 300 and pin 170. FIG. 7A shows valve 250 in its normally closed position. FIG. 7B shows valve 250 when shrinkage of temperature sensitive element 370, caused by exposure to high temperature, caused valve 250 to move into an open position. It will be appreciated that temperature sensitive element 370 may be fixed to pin 170 in numerous ways. For example, element 370 may be fixed to a notch (not shown) in the lower part of pin 170 or may be otherwise adhered or attached to pin 170. Similarly, element 370 may be attached to bracket 370 in numerous ways. For example, element 370 may be looped over an end of bracket 300, may be clamped, crimped, or anchored to bracket 300, or may be otherwise attached or adhered to bracket 300.

Figure 8A:
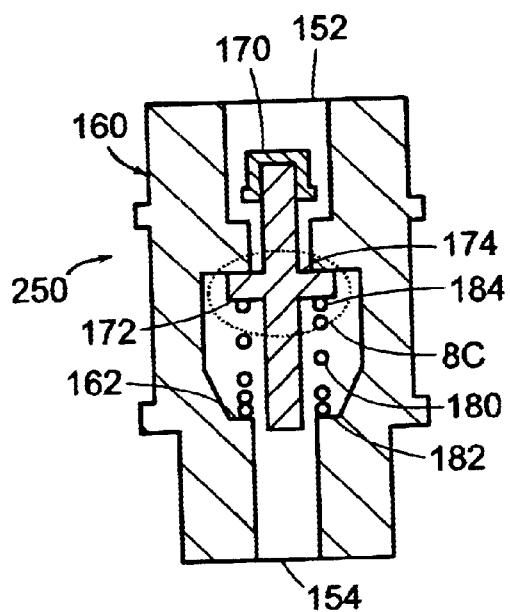
FIG. 8A shows a sectional view of another embodiment of an inflation valve constructed according to the invention in its normally closed position.
Figure 8B:
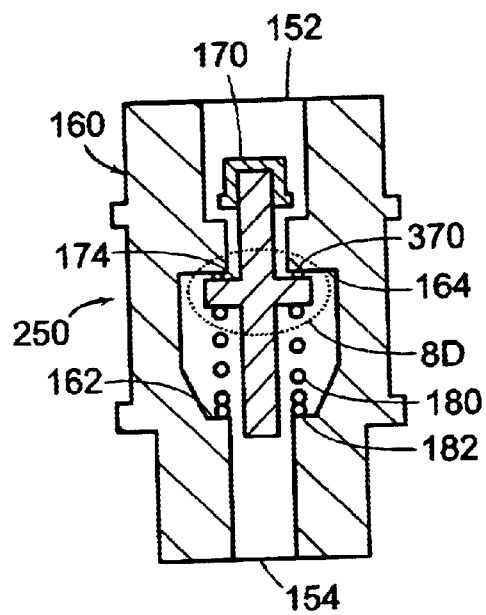
FIG. 8B shows a sectional view of the valve shown in FIG. 8A in an open position.

FIGS. 8A and 8B illustrate yet another embodiment of a valve 250 constructed according to the invention. FIG. 8A shows valve 250 in its normally closed position. FIG. 8B shows valve 250 in an open position. In this embodiment, temperature sensitive elements 370 expand upon exposure to increased temperature and force shoulders 174 (of pin 170) and 164 (of body) apart to thereby open the valve.

Figure 8D:
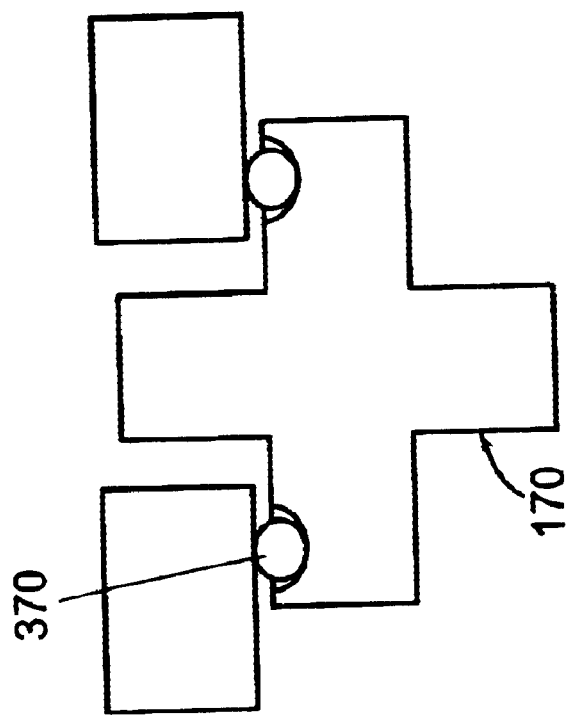
FIG. 8D shows a magnified view of a portion of the pin and body enclosed within the ellipse 8D as shown in FIG. 8B.
Figure 8C:
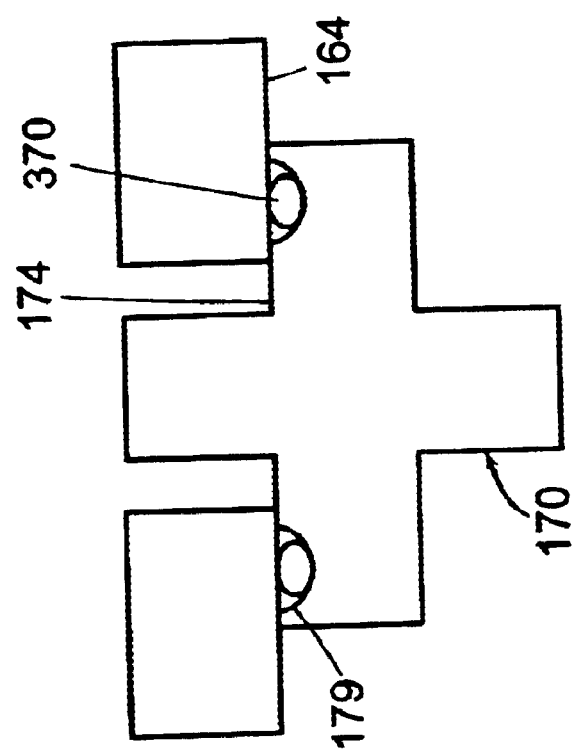
FIG. 8C shows a magnified view of a portion of the pin and body enclosed within the ellipse 8C as shown in FIG. 8A.

FIG. 8C shows a magnified view of the portion of pin 170 and body 160 enclosed within the ellipse 8C as shown in FIG. 8A. Similarly, FIG. 8D shows a magnified view of the portion of pin 170 and body 160 enclosed within ellipse 8D as shown in FIG. 8B. As shown in FIGS. 8C and 8D, in this embodiment, shoulder 174 of pin 170 defines one or more wells, or recesses, 179. Temperature sensitive elements 370 are disposed in the wells 179. At normal room temperatures, temperature sensitive elements are sufficiently small to fit within the wells 179 so that contact between shoulders 174 (of pin 170) and 164 (of body) form a seal and effectively close valve 250. However, when the ambient temperature increases above a selected value (e.g., seventy or ninety degrees Celsius), temperature sensitive elements 370 expand beyond wells 179 and force shoulders 174 and 164 apart thereby opening valve 250. In this embodiment, temperature sensitive elements 370 may be manufactured from plastic materials with relatively high coefficients of thermal expansion such as nylon or low density polyethylene or metallic materials with high coefficients of thermal expansion such as zinc, lead, magnesium, aluminum, tin, and their alloys.

Figure 1:
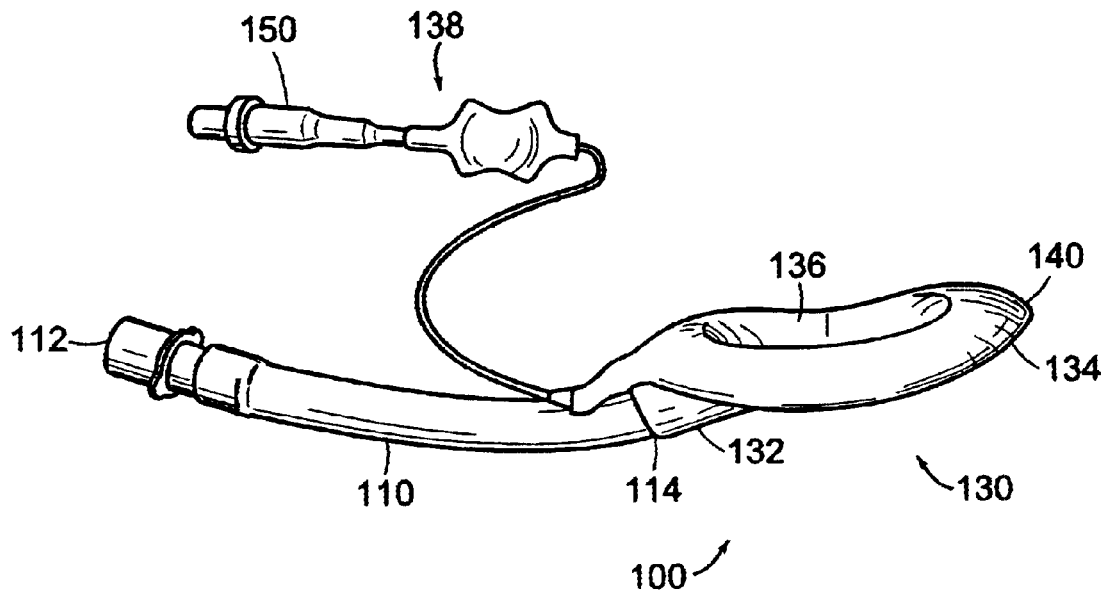
FIG. 1 shows a prior art laryngeal mask airway device.
Figure 9:
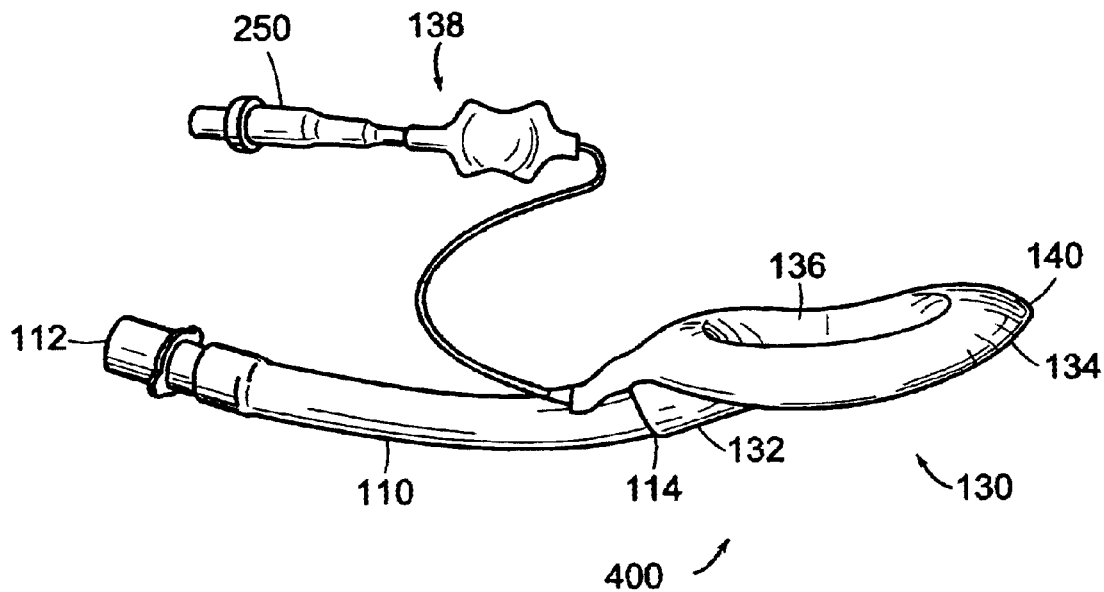
FIG. 9 shows a laryngeal mask airway device constructed according to the invention.

FIG. 9 shows a laryngeal mask airway device 400 constructed using valve 250 according to the invention. The valve 250 used in device 400 may be any of the valves explicitly disclosed herein or any other valve that automatically opens at high temperatures. In operation, valve 250 permits laryngeal mask airway device 400 to be inflated and deflated in its customary fashion (e.g., by coupling an air syringe to an end of valve 250), and device 400 may be used with patients in the customary fashion. However, when device 400 is exposed to high temperatures (e.g., in the sterilizing environment of an autoclave), valve 250 automatically opens thereby advantageously allowing any gas trapped in inflatable device 400 to escape. Valve 250 may be used with any inflatable medical device such as a laryngeal mask airway device, an endotracheal tube, or a tracheostomy tube. Also, in addition to airway type medical devices, valve 250 may also be used with other types of inflatable medical devices such as balloon catheters (e.g., such as angioplasty catheters or other cardiac catheters). It will be appreciated that valve 250 may be used with any inflatable medical device to protect the device from excessive expansion during sterilization.

Since certain changes may be made in the above apparatus without departing from the scope of the invention herein involved, it is intended that all matter contained in the above description or shown in the accompanying drawing shall be interpreted in an illustrative and not a limiting sense. For example, valves constructed according to the invention have been discussed as including prior art valves 150 of the type illustrated in FIGS. 2A–2E. However, it will be appreciated that valve 150 is merely exemplary and that the invention encompasses inflatable devices constructed using any valve that automatically opens at high temperature. Valves have also been discussed herein as preventing fluid from flowing through the valve when in the closed position. It will be appreciated that any valve will leak by some amount even when in the closed position and that phrases such as "preventing fluid from escaping" or "preventing fluid from flowing" do not imply that a closed valve prevents all leakage and merely means that a closed valve provides more resistance to fluid flow than does an open valve.

What is claimed is:

1. A laryngeal mask airway device, comprising:
   A. an airway tube, the airway tube extending from a proximate end to a distal end;
   B. an inflatable mask portion fixed to the airway tube, the mask portion being insertable through the mouth of a patient to an inserted location within the patient, the mask portion forming a seal around the patient's glottic opening when the mask portion is in the inserted location and inflated, the proximate end of the airway tube being disposed outside the patient when the mask portion is in the inserted location;
   C. a valve in fluid communication with the inflatable mask portion, the valve including a member that is movable between an open position and a closed position, the valve preventing fluid from escaping the mask portion when the member is in the closed position, the valve permitting fluid to escape the mask portion when the member is in the open position, the valve including a resilient element, the resilient element providing a first force that biases the member towards the closed position, the valve including a temperature sensitive element, the temperature sensitive element generating a second force that biases the member towards the open position, the first force being greater than the second force when the ambient temperature is below a first value, the first force being smaller than the second force when the ambient temperature is above a second value, an end portion of the member being accessible to an environment external to the valve, the member being movable to the open position by applying pressure to the end portion of the member.

2. A device according to claim 1, the second force being substantially equal to zero when the ambient temperature is below the first value.

3. A device according to claim 1, the temperature sensitive element comprising a nickel titanium alloy.

4. A device according to claim 1, the temperature sensitive element being characterized by a first length when the ambient temperature is below the first value, the temperature sensitive element being characterized by a second length when the ambient temperature is above the second value, the first length being longer than the second length.

5. A device according to claim 1, the valve including a body, the body defining an internal passage that extends through the body.

6. A device according to claim 5, the body further defining a first shoulder.

7. A device according to claim 6, the member defining a second shoulder, the first and second shoulders being in contact when the member is in the closed position, the first and second shoulders being spaced apart when the member is in the open position.

8. A device according to claim 7, further including a cap fixed to one end of the body.

9. A device according to claim 8, further including a post fixed to one end of the member.

10. A device according to claim 9, the temperature sensitive element having a first end, a second end, and a central portion, the first and second ends of the temperature sensitive element being fixed to the cap, the central portion of the temperature sensitive element contacting the post.

11. A device according to claim 10, the post defining a slot, the central portion of the temperature sensitive element extending through the slot.

12. A device according to claim 8, the cap including a base, a body, and at least one clamp.

13. A device according to claim 12, the clamp being disposed between a portion of the base and a portion of the body.

14. A device according to claim 13, an end of the temperature sensitive element being fixed to the clamp.

15. A device according to claim 5, the member being disposed in the internal passage.

16. A device according to claim 15, an end of the member being proximate to an open end of the valve.

17. A device according to claim 1, the second value being greater than or equal to seventy degrees Celsius.

18. A medical device, comprising:
   A. a tube defining an interior passage;
   B. an inflatable structure fixed to the tube, the inflatable structure being insertable into an airway of a human patient, the inflatable structure forming a seal with a portion of the airway when inserted into the patient and inflated;
   C. an inflation lumen having a first end and a second end, the first end of the inflation lumen being coupled to the inflatable structure;
   D. a valve coupled to the second end of the inflation lumen, the valve defining a closed position and an open position, a fluid flow path being provided when the valve is in the open position, the fluid flow path extending from an interior of the inflatable structure through the inflation lumen and through the valve, the valve blocking the fluid flow path when the valve is in the closed position, the valve including a temperature sensitive element, the temperature sensitive element forcing the valve into the open position when a temperature exceeds a first value, the temperature sensitive element allowing the valve to return to the closed position when the temperature falls below a second value.

19. A device according to claim 18, the valve including a movable member and a body, a first surface of the movable member contacting a second surface of the body when the valve is in the closed position, the first surface of the movable member being spaced apart from the second surface of the body when the valve is in the open position.

20. A device according to claim 19, the valve including a spring, the spring biasing the first surface of the movable member towards the second surface of the body.

21. A method of automatically protecting an inflatable device during sterilization, the method comprising:
   A. providing the device with a temperature sensitive valve that automatically opens when a temperature exceeds a first value;
   B. exposing the device to an environment that will sterilize the device, the environment being characterized by a temperature above the first value, the valve automatically opening and permitting fluid in the inflatable device to escape into the environment.

22. A medical device, comprising:
   A. an inflatable structure configured for positioning in a human patient;
   B. a valve in fluid communication with the inflatable structure, the valve including a member that is movable between an open position and a closed position, the valve preventing fluid from escaping the inflatable structure when the member is in the closed position, the valve permitting fluid to escape the inflatable structure when the member is in the open position, the valve including a resilient element, the resilient element providing a first force that biases the member towards the closed position, the valve including a temperature sensitive element, the temperature sensitive element generating a second force that biases the member towards the open position, the first force being greater than the second force when the ambient temperature is below a first value, the first force being smaller than the second force when the ambient temperature is above a second value, an end portion of the member being accessible to an environment external to the valve, the member being movable to the open position by applying pressure to the end portion of the member.

23. A medical device according to claim 22, the second force being substantially equal to zero when the ambient temperature is below the first value.

24. A medical device according to claim 22, the temperature sensitive element comprising a nickel titanium alloy.

25. A medical device according to claim 22, the temperature sensitive element being characterized by a first length when the ambient temperature is below the first value, the temperature sensitive element being characterized by a second length when the ambient temperature is above the second value, the first length being longer than the second length.

26. A medical device according to claim 22, the valve including a body, the body defining an internal passage that extends through the body.

27. A medical device according to claim 26, the body further defining a first shoulder.

28. A medical device according to claim 27, the member defining a second shoulder, the first and second shoulders being in contact when the member is in the closed position, the first and second shoulders being spaced apart when the member is in the open position.

29. A medical device according to claim 28, further including a cap fixed to one end of the body.

30. A medical device according to claim 29, further including a post fixed to one end of the member.

31. A medical device according to claim 30, the temperature sensitive element having a first end, a second end, and a central portion, the first and second ends of the temperature sensitive element being fixed to the cap, the central portion of the temperature sensitive element contacting the post.

32. A medical device according to claim 31, the post defining a slot, the central portion of the temperature sensitive element extending through the slot.

33. A medical device according to claim 29, the cap including a base, a body, and at least one clamp.

34. A medical device according to claim 33, the clamp being disposed between a portion of the base and a portion of the body.

35. A medical device according to claim 34, an end of the temperature sensitive element being fixed to the clamp.

36. A device according to claim 22, the second value being greater than or equal to seventy degrees Celsius.

* * * * *